(12) United States Patent
Dusenbery et al.

(10) Patent No.: US 7,086,404 B2
(45) Date of Patent: Aug. 8, 2006

(54) SURGICAL DRAPE WITH ADJUSTABLE FENESTRATION

(75) Inventors: Casey L. Dusenbery, Roswell, GA (US); Christopher D. Fenwick, Alpharetta, GA (US)

(73) Assignee: Kimberly-Clark Worldwide, Inc., Neehan, WI (US)

( * ) Notice: Subject to any disclaimer, the term of this patent is extended or adjusted under 35 U.S.C. 154(b) by 0 days.

(21) Appl. No.: 11/010,489

(22) Filed: Dec. 13, 2004

(65) Prior Publication Data

US 2006/0124138 A1 Jun. 15, 2006

(51) Int. Cl.
  A41D 13/12 (2006.01)

(52) U.S. Cl. ........................ 128/853; 128/849

(58) Field of Classification Search .............. 129/849, 129/850, 851, 852, 853, 854, 855, 856
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,669,106 A | 6/1972 | Schrading et al. | |
| 3,692,618 A | 9/1972 | Dorschner et al. | |
| 3,802,817 A | 4/1974 | Matsuki et al. | |
| 3,942,523 A * | 3/1976 | Rudtke | 128/853 |
| 4,041,203 A | 8/1977 | Brock et al. | |
| 4,100,324 A | 7/1978 | Anderson et al. | |
| 4,323,062 A * | 4/1982 | Canty | 128/852 |
| 4,340,563 A | 7/1982 | Appel et al. | |
| 4,818,464 A | 4/1989 | Lau | |
| 5,145,727 A | 9/1992 | Potts et al. | |
| 5,169,706 A | 12/1992 | Collier, IV et al. | |
| 5,178,931 A | 1/1993 | Perkins et al. | |
| 5,188,885 A | 2/1993 | Timmons et al. | |
| 5,441,056 A * | 8/1995 | Weber et al. | 128/849 |
| 6,298,855 B1 * | 10/2001 | Baird | 128/849 |
| 6,843,252 B1 * | 1/2005 | Harrison et al. | 128/849 |

* cited by examiner

Primary Examiner—Henry Bennett
Assistant Examiner—Camtu Nguyen
(74) Attorney, Agent, or Firm—James B. Robinson; Scott B. Garrison

(57) ABSTRACT

A surgical drape for covering a patient during a surgical procedure is provided. The drape has a base sheet having an upper surface, a lower surface, and a plurality of edges. A fenestration is formed in the base sheet positionable over the surgical site. A reinforcement panel having an upper surface, a lower surface, and a periphery is also provided. The lower surface of the reinforcement panel has a pressure sensitive adhesive applied thereto. The panel is adjustably manipulated and adhered by the pressure sensitive adhesive so as to occlude a portion of the fenestration in the base sheet at the time of the surgical procedure.

10 Claims, 2 Drawing Sheets

SURGICAL DRAPE WITH ADJUSTABLE FENESTRATION

BACKGROUND OF THE INVENTION

The present invention relates generally to surgical drapes, and more particularly to surgical drapes provided with adjustable openings through which surgical procedures are capable of being performed.

Drapes are used during surgical procedures to create and maintain a sterile environment about the surgical site. Draping materials are selected to create and maintain an effective barrier that minimizes the passage of microorganisms between non-sterile and sterile areas. To be effective, a barrier material should be resistant to blood, aqueous fluid, and abrasion, as lint-free as possible, and drapeable. When used during surgery, drapes prevent blood and other bodily fluids from contaminating the sterile field.

A variety of surgical drapes exist, but most share several common features. Most drapes are made of a water-repellent or water-impermeable material, or are coated with such a material, to prevent the passage of bodily fluids as well as contaminating microorganisms. Many of today's surgical drapes are made of disposable nonwoven fabrics, plastic film, or papers.

Surgical drapes will commonly have an opening or aperture (more commonly known in the medical field as a "fenestration") through which the surgical procedure is performed. Typically these fenestrations are sized for specific surgical procedures thus necessitating the creation of multiple drapes, each having appropriately sized fenestrations.

An adhesive material may be attached to the periphery of the drape material about the fenestration to hold the drape in place around the surgical site and to minimize the passage of blood between the drape and the patient's body. The combination of the drape itself and the adhesive material around the perimeter of the aperture ensures a barrier between the surgical wound and the remainder of the body. Some drapes utilize incise materials which extend over the fenestration. The incise materials are typically transparent plastic films having an adhesive side which adheres to the surgical site of the patient. In such draping systems, the drape is secured to the patient by at least the incise material.

One issue faced with current drapes is that they do not allow for the surgical team to adjust the fenestration without resorting to cutting or otherwise damaging the drape. What is needed is a drape that would allow the surgical team to customize the fenestration for each patient or surgeon's needs. The solution should be an improvement over the use of towels. Presently, surgeons place towels over a portion of the fenestration to meet this need. However towels potentially introduce lint to the operating arena and are difficult to keep sterile.

SUMMARY OF THE INVENTION

In response to the foregoing problems and difficulties encountered by those of skill in the art, the present invention is directed toward a surgical drape for covering a patient during a surgical procedure. The drape includes a base sheet having an upper surface, a lower surface, and a plurality of edges. The drape of the present invention further includes a fenestration that is formed in the base sheet through which a surgical procedure may be performed when the drape is covering a patient. An incise layer may be provided, the incise layer being disposed over the fenestration. The incise layer may include an adhesive side that is adapted to adhere to the patient when the drape is covering the patient. In some procedures, particularly those procedures which take a long time, it may be beneficial for the incise layer to be "breathable" by exhibiting high moisture vapor transmission rates. Thus, the adhesive side of the incise layer faces downwardly when the drape is positioned over the patient. Release layers may be provided on the adhesive side of the incise layer to permit easy handling and maintain sterility of the incise layer.

A reinforcement panel is also provided. The reinforcement panel would also have an upper surface, a lower surface, and a periphery. The lower surface would have a pressure sensitive adhesive applied thereto. The panel would also be capable of being adjustably manipulated by the surgical team then adhered by the pressure sensitive adhesive to the drape, the patient, or another surface so as to occlude a portion of the fenestration in the base sheet. More than one reinforcement panel may be provided. The panels may be rectilinear, curvilinear, or some other shape. In certain embodiments they may be disposed over a portion of the fenestration in a reverse mirror image of one another.

Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

Figure 1:
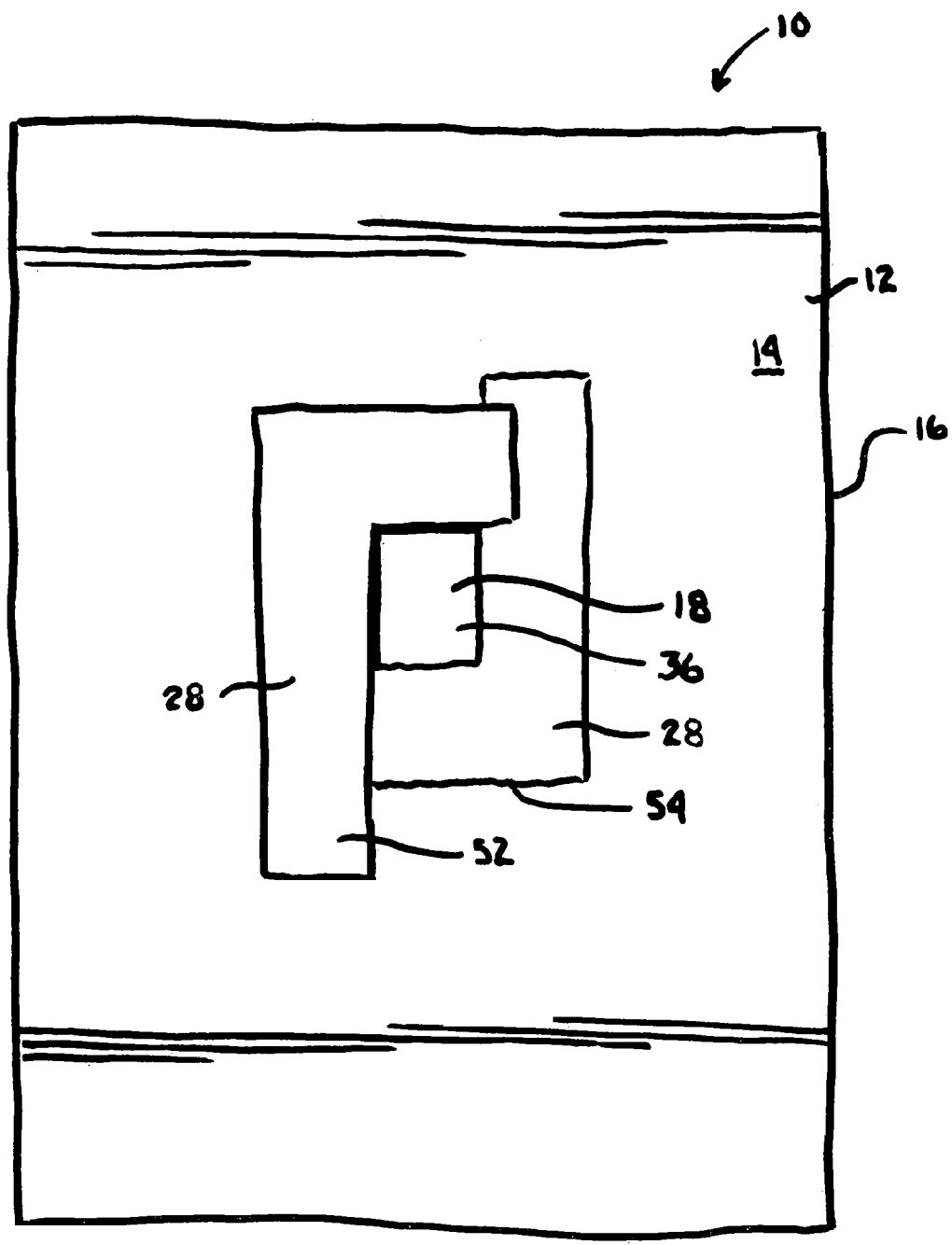
FIG. 1 is a top view of an embodiment of the drape according to the present invention.
Figure 2:
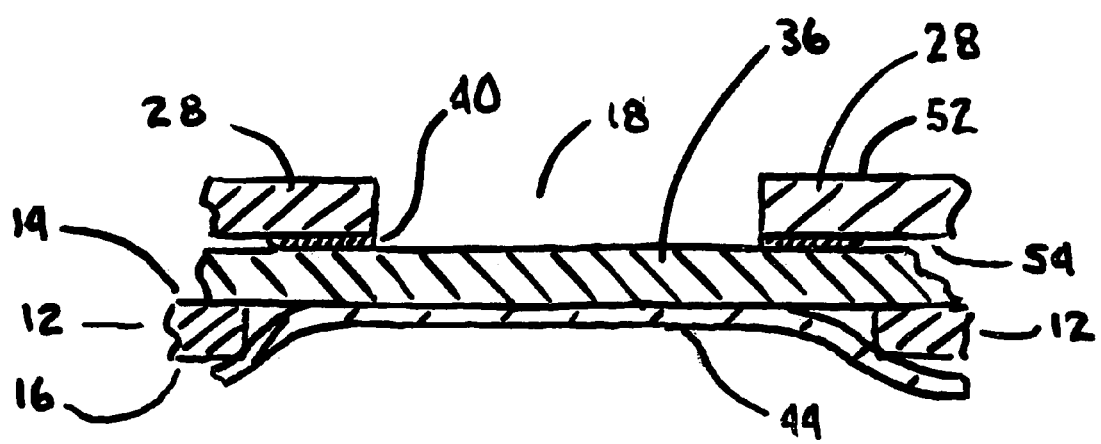
FIG. 2 is a cross-sectional view of the embodiment of the drape depicted in FIG. 1.

In response to the foregoing challenges that have been experienced by those of skill in the art, the present invention is directed toward a drape with an adjustable reinforcement material suitable for use in surgical procedures. The surgical drape 10 of the present invention is illustrated in FIGS. 1 and 2 and includes a base sheet 12 having an upper surface 14 and a lower or patient-contacting surface 16. Although it may have varying dimensions and shapes, drape 10 is normally rectangular and depending upon the procedure to be performed is often sized to cover at least a majority of a patient's body during the surgical procedure.

The base sheet 12 may be made from a wide variety of materials, including, for example, woven, reusable fabrics and nonwoven disposable fabrics or webs. Nonwoven materials suitable for use with the present invention include, for example, multilayer laminates such as a spunbonded/meltblown/spunbonded ("SMS") material. An example of a suitable fabric is disclosed in U.S. Pat. No. 4,041,203, which is hereby incorporated by reference.

As used herein the term "nonwoven fabric or web" means a web having a structure of individual fibers or threads that are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

As used herein "multilayer lanunate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films or coform materials, e.g. SMMS, SM, SFS, etc.

As used herein, the term "coform" means a process in which at least one meltblown diehead is arranged near a chute through which other materials are added to the web while it is forming.

Such other materials may be pulp, superabsorbent particles, cellulose or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

Referring again to FIGS. 1 and 2, the base sheet 12 is shown therein and includes at least one fenestration 18 depicted as being rectangular in shape. However, it should be noted that it is contemplated that the fenestrations utilized in the present invention may have various other shapes as well. Regardless of its actual configuration the fenestration 18 is positioned within the base sheet 12 so that, when the drape 10 is applied to the patient, the fenestration 18 is disposed over the surgical site.

An incise layer 36 may be provided and positioned over the fenestration 18. The incise layer 36 may be secured to the upper surface 14 or the lower surface 16 of the base sheet 12. The incise layer 36 may include an adhesive side that is adapted to adhere to the patient when the drape is covering the patient. Thus, the adhesive side of the incise layer faces downwardly when the drape is positioned over the patient to provide a seal around the surgical site.

The incise layer 36 may be formed from a low-density polyethylene film with adhesive on one side. For example, the incise layers may be constructed of polyethylene film available from Bertek Inc., St. Albans, Vt. 05478, or from a film available from Medical Concepts Development, Inc., St. Paul, N. Mex. 55125.

In other embodiments, strips of adhesive may be positioned around the periphery of the fenestration 18 to adhere the periphery of the fenestrations to the patient. The tacky and pressure-sensitive adhesives used may be of any biologically acceptable adhesive. Examples of such adhesive materials are described in U.S. Pat. No. 3,669,106 entitled "Surgical Drape with Adhesive Attachment Means" to Schrading et. al, which is incorporated herein in its entirety by reference.

To facilitate handling of the drape 10 and to maintain the sterility of the incise layer or, in selected embodiments, the peripheral adhesive strips, the adhesive surface may be covered with a release liner 44. The release liner 44 may be formed of any of a wide variety of materials which are commonly available. For example, wax- or silicone-coated papers may be placed over the adhesive side of the incise layer 36 until the drape 10 is applied to the patient. Alternate materials may also be utilized, such as, for example, plastic materials having at least one non-adherent surface. Such materials may be utilized when a tear-resistant release liner is appropriate.

In some embodiments, the release liner may be segmented to facilitate application of the drape 10 to the patient. For example, the medical personnel applying the drape 10 to the patient may remove one segment of the release liner at a time thus enabling the medical personnel to handle a smaller exposed area of adhesive at one time, reducing the opportunities for contamination or creasing of the exposed incise layer. Additionally, the segmented release liner permits the medical personnel to determine, for each patient and/or type of surgical procedure, the length of the incise layer that must be secured to the patient. For example, a smaller patient may only need one or two of the release liners removed from the incise layer.

As may be seen on FIGS. 1 and 2, a reinforcing absorbent panel 28 is shown as being superimposed on and affixed in some manner, for example, to the upper surface 14 of base sheet 12. In the FIGs., two such panels 28 are depicted as partially overlapping and will be described in more detail below. At any rate, each reinforcing panel 28 may be formed from a variety of materials, including a multi-layer laminate which includes a fluid-absorbing material that may be backed by a fluid-repellant or fluid-impervious film layer. The film-layer side or lower surface 54 of each panel 28 is secured, for example, to the upper surface 14 of base sheet 12.

A variety of attachment mechanisms may be used to secure each panel 28 to the upper surface 14 of the base sheet 12, such as, for example, an adhesive 40 including but not limited to a pressure sensitive adhesive and an adhesive tape located on lower surface 54 of each panel 28, best seen in FIG. 2. Upon securing each panel 28 into its desired position, the absorbent upper surface 52 of each panel 28 remains at least partially exposed and available to absorb fluids emitted from the surgical site. The fluid-impervious film layer, if provided, minimizes the passage of blood and other body fluids through the reinforcing panel 28 and the base sheet 12. Although many commercially available materials are suitable for use in constructing the reinforcing panels 28, an exemplary material is available from Kimberly-Clark Corporation and is marketed under the trade name CONTROL PLUS®.

In some embodiments, the upper surface 52 of the reinforcing panels 28 may have an increased coefficient of friction to provide a slip-resistant surface to lessen the likelihood of undesired movement of surgical instruments that are placed upon the reinforcing panels 28. Each reinforcing panel 28 may be constructed of a material that has an absorbent upper surface to absorb fluids near the operative site. Each reinforcing panel 28 also helps to inhibit penetration of the drape 10 by instruments that are placed on top of the reinforcing panel 28 during surgery.

As shown in FIGS. 1 and 2, the reinforcing panel 28 may be adjustably manipulated by the surgical team to partially occlude a portion of the fenestration 18. As such, the fenestration may be made oversize with respect to the procedure to be performed. By providing a pair of the reinforcement panels 28, the surgical team is capable of manipulating them into position leaving just enough of the fenestration clear to maximize access to the surgical site. As stated above, each panel 28 is provided with a means to secure it in place once positioned. For example, an adhesive may be used for this purpose. Such an adhesive may include, but is certainly not limited to a pressure sensitive adhesive and/or an adhesive tape. The adhesive would for example be disposed upon the lower surface 54 of each panel. The adhesive would enable the panel 28 to be adhered to the base sheet 12, the patient, a corresponding panel 28, as well as to the incise material 36 if present. Placing the adhesive along the periphery of the panel would provide a sealing mechanism redirecting fluid to the upper surface of the reinforcement panel where it can be absorbed or otherwise collected.

One embodiment using a pair of reinforcing panels 28 may be to configure each panel as an L-shaped component. As depicted, the panels 28 may be arranged in a reverse mirror image of one another. This will enable the surgical team to customize the opening through which the surgical procedure is to be performed and to have at least a portion of a reinforcement panel disposed about the periphery of the fenestration. Other arrangements include but are not limited to other rectilinear or curvilinear shapes. Such shapes would be understood by those skilled in the art. Moreover, as stated earlier, a single reinforcement panel or more than two reinforcement panels may be used as well, each capable of being positioned to occlude a portion of the fenestration Though not shown, at least one pouch may be attached to the base sheet 12. The pouch may be utilized to hold surgical instruments, collect fluids or a variety of other similar functions. The pouch may be adhered to the base sheet 12 by adhesive such as tape and the like, stitching, or other commonly known attachment mechanisms. Such a pouch and its method of attachment and use would be known and understood by those skilled in the art. In some embodiments two or more of such pouches may be provided, for example, one pouch being positioned on each side of the fenestration 18. The pouch may be formed of a material that is impervious to liquids, such as, for example, polyethylene or the like. The material may be formed of a transparent or opaque material depending upon the needs required to be met.

As used herein and in the claims, the term "comprising" is inclusive or open-ended and does not exclude additional unrecited elements, compositional components, or method steps.

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

We claim:

1. A surgical drape for covering a patient during a surgical procedure, the drape comprising:
    a base sheet having an upper surface, a lower surface, and a plurality of edges;
    a single fenestration formed in the base sheet positionable over the surgical site; and
    a reinforcement panel having an upper surface, a lower surface, and a periphery, the lower surface having a pressure sensitive adhesive applied to a portion thereof, the panel being adjustably manipulated in the plane of the base sheet and adhered by the pressure sensitive adhesive so as to occlude a portion of the fenestration in the base sheet.

2. The drape of claim 1 wherein the reinforcement panel comprises a rectilinear shape.

3. The drape of claim 1 wherein the reinforcement panel comprises a curvilinear shape.

4. The drape of claim 1 wherein the reinforcement panel is adhered to at least one of an incise material disposed over the fenestration, the base sheet, or a portion of the surgical site.

5. The drape of claim 1 comprising a plurality of such reinforcement panels.

6. The drape of claim 1 comprising two reinforcement panels disposed over a portion of the fenestration in a reverse mirror image of one another.

7. The drape of claim 1 wherein the pressure sensitive adhesive forms a seal at the lower surface of the reinforcement panel directing any liquid onto the upper surface of the reinforcement panel.

8. The drape of claim 7 wherein the reinforcement panel is liquid absorbent.

9. The drape of claim 1 comprising a pair of reinforcement panels at least partially adhered to one another and disposed over the fenestration in the base sheet so as to reduce the visible portion of the fenestration.

10. The drape of claim 1 wherein the pressure sensitive adhesive comprises a tape disposed about the periphery of the reinforcement panel.

* * * * *